(12) United States Patent
Yajima et al.

(10) Patent No.: US 6,726,926 B2
(45) Date of Patent: Apr. 27, 2004

(54) GENE-ENTRAPPED LIPOSOMES PREPARATION AND PROCESS FOR THE PREPARATION THEREOF

(75) Inventors: Haruyoshi Yajima, Fujieda (JP); Keizo Sakuda, Fujieda (JP); Hideshi Ideno, Fujieda (JP); Kunio Yagi, Nagoya (JP); Nobuko Ohishi, Inuyama (JP); Jun Yoshida, Nagoya (JP)

(73) Assignees: Kaken Pharmaceutical Co., Ltd., Tokyo (JP); Institute of Applied Biochemistry, Gifu (JP)

( * ) Notice: Subject to any disclaimer, the term of this patent is extended or adjusted under 35 U.S.C. 154(b) by 0 days.

(21) Appl. No.: 09/790,727

(22) Filed: Feb. 23, 2001

(65) Prior Publication Data

US 2002/0044958 A1 Apr. 18, 2002

(30) Foreign Application Priority Data

Feb. 23, 2000 (JP) .......................... 2000-045894
Jan. 16, 2001 (JP) .......................... 2001-007758

(51) Int. Cl.[7] .............................................. A61K 9/127
(52) U.S. Cl. ........................... 424/450; 264/4.1; 514/44
(58) Field of Search .................. 424/450; 435/174–177; 264/4.1; 514/44; 428/402.2

(56) References Cited

U.S. PATENT DOCUMENTS 4,880,635 A * 11/1989 Janoff et al. ................. 424/450
5,552,157 A * 9/1996 Yagi et al. .................... 424/450

* cited by examiner

*Primary Examiner*—Dave T. Nguyen
*Assistant Examiner*—Jan Eric Angell
(74) *Attorney, Agent, or Firm*—Rader, Fishman & Grauer PLLC

(57) ABSTRACT

It provides a gene-entrapping liposome preparation which can be preserved over a long period of time, and a process for the preparation of the same. The preparation can be prepared by adding an aqueous solution of disaccharide to gene-entrapping liposomes. The frozen preparation can be preserved for 6 months or more at preservation temperature of −20° C., and the preparation shows excellent restoration ability in water and does not show reduction in biological activity. In the case of the lyophilized preparation, it can be preserved for longer time of about 1 year, shows excellent restoration ability in water, and does not show reduction in biological activity.

5 Claims, No Drawings

GENE-ENTRAPPED LIPOSOMES PREPARATION AND PROCESS FOR THE PREPARATION THEREOF

BACKGROUND OF THE INVENTION

1. Field of the Invention

The present invention relates to a gene-entrapping liposome preparation and a process for the preparation thereof and more particularly, to the preparation which can be preserved over an extended period of time as well as the process for the preparation of same.

2. Related Arts

Liposomes have been expected as an actual preparation for gene therapy as quality control using liposomes is easier to manage than other gene therapy methods such as using a virus as a vector for introducing a gene, and the high degree of safety inherent in liposome methods. However, a plasmid DNA entrapped in liposomes shows low stability in a solution, and thus recent trends on study of liposomes have been occupied by a DNA/Lipids Complex method, wherein a solution containing gene recombinant plasmid DNA and a lipid solution for forming the liposomes are charged in a separate vial and then the plasmid DNA and lipids are mixed for preparing a required preparation, at the time of using the preparation.

The DNA/Lipids Complex method has disadvantages as it is difficult to prepare a uniform preparation, since the process for preparation is somewhat complicated. Therefore, there is great demand for a liposome preparation for gene therapy, which shows excellent stability in preservation, is easy in preparation at the time of using, and is constant in quality. It has been known that such multilamellar liposomes show higher gene entrapping efficiency, good expression of the gene and lower toxicity to cells and thus are useful as the vector for gene therapy in its effectiveness and safety. Their constitutive lipids are N-(α-trimethyl ammonioacetyl)-didodecyl-D-glutamate chloride (TMAG), dilauroyl phosphatidylcholine (DLPC) and dioleoyl phosphatidyl ethanolamine (DOPE) and a molar ratio of the lipids is 1:2:2 [Japanese Patent 4-108391(A)]. However, the liposomes are not suitable for preservation over long period of time, since decomposition of DNA is apt to be caused, when the liposome preparation is preserved in a solution. An improvement per se in stability of DNA is possible by freezing the solution of liposomes entrapping the DNA, but there is a disadvantage that aggregation of the liposomes occurs during the freezing period of time, uniformity of the liposome in the defrosted solution at the time of using the same is spoiled, and thus biological activity of the liposome preparation becomes low.

Control of diameter of the liposomes is an important factor for carrying out gene therapies, since gene-entrapping liposomes having smaller diameter give toxicity to cells and larger liposomes show lower delivery efficiency of the entrapped gene to cells.

SUMMARY OF THE INVENTION

Therefore, an object of the invention is to provide a gene-entrapping liposome preparation which shows high gene catching efficiency, good expression of the gene, low toxicity to cells, high safety in use, excellence in stability during preservation, ease in conversion of form from preservation state to dosing state at the time of using, and substantially no reduction in biological activity during the conversion of form, as well as a process for the preparation of the gene-entrapping liposome preparation.

The inventors have intensively studied and investigated for overcoming the aforesaid problems. More particularly, the present invention is directed to liposomes obtained by adding an aqueous solution of a disaccharide to gene-entrapping liposomes and then freezing or lyophilized the solution containing the liposomes, to accomplish good restoration when the frozen or lyophilized liposomes are defrosted or suspended in water after preservation, and where a remarkable change in diameter cannot be recognized. Thus the liposomes do not cause aggregation thereof during the freezing and defrosting or lyophilizing and hydrating period and the gene-entrapping liposomes are excellent in expression of the gene DNA.

Therefore, the gene-entrapping liposome preparation which can be preserved over long period of time according to the invention is characterized by a frozen or lyophilized product containing the gene-entrapping liposomes and a disaccharide as a protector.

The process for the preparation of the gene-entrapping liposome preparation which can be preserved over long period of time according to the invention is characterized by adding an aqueous solution of disaccharide to the gene-entrapping liposomes and freezing or lyophilizing the same.

MANNERS FOR CARRYING OUT THE INVENTION

In the invention, it is preferable that constitutive lipids for the liposomes are TMAG, DLPC and DOPE and that molar ratio of the lipids is 1:2:2.

Such disaccharides can be listed as sucrose, trehalose, lactose, xylobiose, xytobiose, levanbiose, bicyanose, sambbiose, melibiose, epicerobiose, turanose, lactulose, rutinose, chondrosine and so on, but it is preferable to select at least one of sucrose and lactose. As an amount of the disaccharide, it is preferable in a range of 300–3333 g to 1 g of the gene which is entrapped in the liposomes, in both the cases of sucrose and lactose.

As mean diameter of the liposome, it is preferable in a range of 0.02–10 µm, and more preferably in a range of 0.6–6 µm.

DETAILED DESCRIPTION OF PREFERRED EMBODIMENT

The invention will be explained in more detail with reference to Test Examples. Followings are materials, process for preparing gene-entrapping liposomes and testing methods and so on used in the Test Examples.

Materials (a) TMAG (manufactured by Sogo Pharmaceutical Co., Ltd.), (b) DLPC (manufactured by Nichiyu Liposome Co., Ltd.), (c) DOPE (manufactured by Nichiyu Liposome Co., Ltd.), (d) Plasmid expressing human interferon β (pDRSV-INF β) The plasmid was cloned by using *E. coli* DH5α and purified by using QIA Ultra 100 kit (manufactured by QIAGEN Company) to obtain the recombinant plasmid, (e) Japanese Pharmacopoeia sucrose (manufactured by Kyowa Hakko Co., Ltd.), (f) Lactose of superior quality (manufactured by Wako Pure Chemical Industries Ltd.), (g) Japanese Pharmacopoeia lactose (manufactured by Iwaki Co., Ltd), (h) Japanese Pharmacopoeia sorbitol (manufactured by Junsei Kagaku Co., Ltd.), (i) Japanese Pharmacopoeia mannitol (manufactured by Kyowa Hakko Co., Ltd.), (j) Xylitol of superior quality (manufactured by Wako Pure Chemical Industries Ltd.), (k) Glucose of superior quality (manufactured by Wako Pure Chemical Industries Ltd.), and (l) Japanese Pharmacopoeia magnesium gluconate (manufactured by Kyowa Hakko Co., Ltd.).

Process for the preparation of gene-entrapping liposomes

Lipids of TMAG, DLPC and DOPE were taken in molar ratio of 1:2:2 to dissolve in chloroform and then the solvent was removed through a condensation and drying in vacua. To this lipid mixture, pDRSV-IFN β and isotonic phosphate buffer (containing sodium chloride 13.7 mmol/l, sodium monohydrogenphosphate 8.7 mmol/l and sodium dihydrogenphosphate 1.4 mmol/l) were added to treat with polytron homogenizer at 15000 rpm and then subjecting to pressure filtration and centrifugal separation to prepare gene-entrapping liposomes. The liposomes contain DNA of about 1.4 mg/ml (measured by an absorption method) and lipid components of about 40 μmol/ml (measured by HPLC), and have mean diameter of 1–2 μm.

Freezing method

A suspension (1 ml portion) containing sucrose and gene-entrapping liposomes was prepared and dispensed into glass vials to freeze the suspension to obtain frozen samples.

Lyophilizing method

Prepared gene-entrapping liposomes (1 ml portion) were dispensed into glass vials and treated by a lyophilizer (manufactured by Kyowa Sinkuu Co., Ltd.) to obtain lyophilized samples.

Stability test

The frozen samples were preserved for 1–6 months at −20° C., subjected to a periodical sampling, and the frozen samples were defrosted at room temperature to carry out tests on the following items:

(1) Measurement of diameter of the liposomes

Mean diameter of the liposomes was measured by using NICOMP M370 Submicronparticlesizer.

(2) Measurement of the amount of DNA remained

After solubilizing the liposomes with 10% Triton X-100, agarose-gel electrophoresis was carried out and ethidium bromide was added to measure fluorometrically an amount of DNA in the band of pDRSV-IFN β. DNA purity is estimated by the ratio of fluorescent intensity in the band of pDRSV-IFN β to the total sum of fluorescent intensities in all bands obtained through the electrophoresis.

The lyophilized samples were preserved in a frozen or refrigerated state at −20, 5 and 10° C., subjected to a periodical sampling, and tests were carried out on the following 4 items: Testing period of time is over 1–6 months or 4–12 months.

(1) Restoration

Distilled water of 1 ml was added to a lyophilized sample in the vial which was allowed to stand for 10 minutes and then shaken by hands to visually observe whether or not the suspension in the vial was uniform.

(2) Measurement of diameter of the liposomes

Mean diameter of the liposomes was measured by using NICOMP M370 Submicronparticlesizer.

(3) Measurement of the amount of DNA remained

After solubilizing the liposomes with 10% Triton X-100, agarose-gel electrophoresis was carried out and ethidium bromide was added to measure purity of DNA from the ratio of fluorescent intensity in the band of pDRSV-IFN β to the total sum of fluorescent intensities in all bands obtained through the electrophoresis. The ratio of DNA remaining was calculated on the basis of the purity of DNA before and after lyophilization.

(4) Expression test of human interferon β

Liposomes diluted by D-MEM medium to a concentration of 15 ng/ml as DNA were added to U251SP strain, human malignant glicoma cells, and cultivated for 2 days at 37° C. to measure an amount of expressed human interferon β by ELISA method.

TEST EXAMPLE 1

Inhibition of liposome aggregation by saccharides

Sucrose of 9 W/V %, lactose of 9 W/V % or mannitol of 5 W/V % as a final concentration was added to said gene-entrapping liposome and then frozen. Each of the frozen samples was defrosted to observe visually the same. As a result, liposome aggregation was recognized only in the case of the sample containing the mannitol, and inhibition of liposome aggregation can be recognized in the case of samples containing sucrose or lactose. Next, concentration of added sucrose and lactose was changed to check its influence on the inhibition of liposome aggregation. Further, the inhibition was checked as to other saccharides and sugaralcohols. In this Test Example, each of the suspensions containing the saccharaide or sugaralcohol and gene-entrapping liposomes [final concentration of pDRSV-IFN β:150 μg/ml, lipids: 6.7 μmol/ml (TMAG:DLPC:DOPE= 1:2:2)] was prepared, frozen, allowed to stand at −20° C. overnight, and defrosted at room temperature to measure the diameter of the liposomes. Results are shown in Table 1. Inhibition of liposome aggregation can be recognized in case of using sucrose, lactose, sorbitol or glucose and good inhibition can be recognized in case of using sucrose of 18 W/V %, lactose of 9 and 14 W/V % or sorbitol of 5 W/V %, as final concentration.

TABLE 1

| Saccharide | Concentration (W/V %) | Mean diameter (μm) |
|---|---|---|
| Sucrose | 4.5 | 4.7 |
| | 9.0 | 4.2 |
| | 18.0 | 2.6 |
| Lactose | 4.5 | 4.8 |
| | 9.0 | 2.6 |
| | 14.0 | 2.6 |
| Sorbitol | 5.0 | 3.7 |
| Xylitol | 4.0 | 10.3 |
| Mannitol | 5.0 | can not be measured |
| Glucose | 5.0 | 5.7 |
| Magnesium gluconate | 5.0 | 6.6 |
| No addition | — | 14.6 |
| Before freezing | — | 1.5 |

TEST EXAMPLE 2

A suspension containing sucrose (final concentration: 9 W/V %) and gene-entrapping liposomes [final concentration of pDRSV-IFN β:150 μg/ml, lipids: 6.7 μmol/ml (TMAG:DLPC:DOPE=1:2*2) was prepared and dispensed in glass vials by 1 ml to freeze the suspension in each vial. The frozen preparations were preserved for 1–6 months at −20° C. During the preservation time of period, samplings were carried out to defrost preparations, and mean diameter and stability of DNA were measured. Results are shown in Tables 2A and 2B. As seen therefrom, change in diameter due to the frozen preservation cannot be recognized, decomposition of DNA was inhibited, and lowering in expressed amount of IFN-β was not recognized.

TABLE 2A

| Preservation temperature | Item of measurement | Before freezing | Just after frozen | After 1 month |
|---|---|---|---|---|
| −20° C. | Mean diameter (μm) | 1.1 | — | 1.3 |
|  | Purity of DNA (%) | 91.3 | — | 94.3 |

TABLE 2B

| Preservation temperature | Item of measurement | After 2 months | After 3 months | After 4 months | After 6 months |
|---|---|---|---|---|---|
| −20° C. | Mean diameter (μm) | 1.5 | 1.4 | 1.4 | 0.9 |
|  | Purity of DNA (%) | 92.1 | 91.0 | 92.5 | 92.7 |

TEST EXAMPLE 3

A suspension containing sucrose (final concentration: 7, 9 or 18 W/V %) and gene-entrapping liposomes [final concentration of pDRSV-IFN β:150 μg/ml, lipids: 6.7 μmol/ml (TMAG:DLPC:DOPE=1:2:2)] was prepared and dispensed in glass vials by 1 ml to lyophilize the suspension in each vial. These lyophilized samples were preserved for 1–6 months at 5° C. During the preservation period of time, each of the sampled preparations was suspended in distilled water to measure mean diameter and check stability of the DNA. Results of measurement on the diameter are shown in Table 3. As seen therefrom, inhibition of liposome aggregation by the sucrose can be recognized in all of its concentrations, and good inhibition can be recognized in the case of 9 and 18 W/V % in the final concentration. Each of the lyophilized samples used in this Test Example shows good restoration in water. Final concentrations of 9 and 18 W/V % of sucrose correspond to 600 and 1200 g based on 1 g of gene entrapped in the liposomes.

TABLE 3

| Concentration of sucrose (W/V %) | Just after prepared | Just after liophilized | After 1 month | After 3 months | After 6 months |
|---|---|---|---|---|---|
| 7 | 1.8 | 3.6 | 4.9 | 5.5 | 2.9 |
| 9 | 1.8 | 1.6 | 1.7 | 1.4 | 1.5 |
| 18 | 2.8 | 2.2 | 1.7 | 1.9 | 1.5 |
| No addition | 1.5 | 0.4 | 14.4 | — | — |
| No addition |  |  |  |  |  |

TEST EXAMPLE 4

Lyophilized samples similar to Test Example 3 were prepared, excepting that the final concentration of lactose of 7, 9 or 14 W/V % was used and tests similar to those in Example 3 were carried out on the samples. Results of measurement on the diameter are shown in following Table 4. As seen therefrom, inhibition of liposome aggregation by the lactose can be recognized in all of its concentrations. Each of the lyophilized samples used in this Test Example shows good restoration in water. Final concentrations of 7, 9 and 14 W/V % of sucrose correspond to 467, 600 and 933 g based on 1 g of gene entrapped in the liposomes.

TABLE 4

| Concentration of sucrose (W/V %) | Just after prepared | Just after liophilized | After 1 month | After 3 months | After 6 months |
|---|---|---|---|---|---|
| 7 | 1.6 | 2.2 | 1.7 | 2.0 | 1.6 |
| 9 | 4.2 | 1.5 | 1.6 | 1.7 | 1.6 |
| 14 | 2.4 | 1.3 | 1.6 | 1.7 | 1.8 |
| No addition | 1.5 | 0.4 | 14.4 | — | — |

TEST EXAMPLE 5

To confirm the usefulness of prescriptions which contain sucrose as the protector, pDRDV-IFN β-entrapped lyophilized liposome preparations with prescriptions shown in Table 5 were prepared and each of the preparations was preserved for 4–12 months at −20° C., and sampling thereof was carried out to suspend in distilled water, measure mean diameter and remaining ratio of DNA. Results are shown in Tables 6 and 7 and in every prescription, inhibition of liposome aggregation and stabilization of DNA are recognized. The gene-entrapping lyophilized liposome preparations according to the invention do not show reduction in the amount of IFN-β expressed, even if the preparations were preserved for 12 months at 10° C. or −20° C., in any case of prescription 1–6 shown in Table 5. When the gene-entrapping liposomes were preserved in a state of solution at 10° C. as a control, the amount of IFN-β expressed reduced, with preserved time. Added amounts of sucrose correspond to 2667 g (Prescription 1), 3000 g (Prescription 2), 1200 g (Prescription 3), 900 g (Prescription 4), 600 g (Prescription 5) and 3333 g (Prescription 6), based on 1 g of the gene entrapped in the liposomes.

TABLE 5

| Prescription | Concentration of sucrose (W/V %) | DNA concentration in liposomes μg/ml (lipid concentration: μmol/ml) |
|---|---|---|
| 1 | 8 | 30 (1.1) |
| 2 | 9 | 30 (1.1) |
| 3 | 9 | 75 (2.9) |
| 4 | 9 | 100 (3.8) |
| 5 | 9 | 150 (5.7) |
| 6 | 10 | 30 (1.1) |

TABLE 6

| Preservation temperature (° C.) | Prescription No. | Mean diameter (μm) | | | | | | |
|---|---|---|---|---|---|---|---|---|
| | | Before liophilization | Just after liophilization | After 4 months | After 6 months | After 8 months | After 10 months | After 12 months |
| 10 | 1 | 1.6 | 1.4 | 1.7 | 1.4 | 2.0 | 1.4 | 1.8 |
| | 2 | 1.4 | 1.7 | 1.7 | 1.7 | 1.6 | 1.4 | 1.2 |
| | 3 | 2.6 | 1.3 | 0.9 | 1.1 | 1.8 | 1.3 | 1.1 |
| | 4 | 1.3 | 1.5 | 1.5 | 1.6 | 1.4 | 1.2 | 1.5 |
| | 5 | 1.3 | 1.3 | 2.0 | 1.5 | 1.8 | 1.4 | 1.5 |
| | 6 | 1.4 | 1.8 | 1.7 | 1.9 | 1.9 | 1.7 | 1.4 |
| −20 | 1 | 1.6 | 1.4 | 1.6 | 1.6 | 1.6 | 1.7 | 1.4 |
| | 2 | 1.4 | 1.7 | 1.8 | 1.4 | 1.3 | 1.4 | 1.1 |
| | 3 | 2.6 | 1.3 | 1.2 | 1.7 | 1.1 | 1.5 | 1.4 |
| | 4 | 1.3 | 1.5 | 1.2 | 1.5 | 1.4 | 1.7 | 1.8 |
| | 5 | 1.3 | 1.3 | 3.6 | 1.7 | 1.6 | 1.8 | 2.2 |
| | 6 | 1.4 | 1.8 | 2.2 | 1.9 | 2.4 | 1.6 | 1.4 |

TABLE 7

| Preservation temperature (° C.) | Prescription No. | Ratio of DNA remained (%) | | | | | |
|---|---|---|---|---|---|---|---|
| | | Before liophilization | After 4 months | After 6 months | After 8 months | After 10 months | After 12 months |
| 10 | 1 | 100 | 102.4 | 101.3 | 99.6 | 100.6 | 100.1 |
| | 2 | 100 | 100.0 | 100.3 | 102.0 | 99.8 | 98.9 |
| | 3 | 100 | 98.8 | 101.9 | 102.8 | 100.8 | 99.3 |
| | 4 | 100 | 98.3 | 98.1 | 98.8 | 98.2 | 99.7 |
| | 5 | 100 | 100.0 | 101.0 | 101.4 | 100.0 | 100.6 |
| | 6 | 100 | 100.2 | 101.4 | 99.3 | 99.8 | 101.9 |
| −20 | 1 | 100 | 99.8 | 102.2 | 101.5 | 95.4 | 101.6 |
| | 2 | 100 | 101.2 | 101.9 | 103.3 | 96.6 | 100.8 |
| | 3 | 100 | 101.9 | 101.6 | 102.1 | 96.7 | 105.8 |
| | 4 | 100 | 101.1 | 99.9 | 99.8 | 99.0 | 100.6 |
| | 5 | 100 | 101.4 | 102.9 | 102.1 | 101.1 | 102.8 |
| | 6 | 100 | 100.2 | 101.7 | 99.4 | 101.3 | 101.0 |
| 10 (In solution) | — | 100 | 62.1 | 49.3 | 41.5 | 34.8 | 24.1 |

TEST EXAMPLE 6

To confirm the usefulness of prescriptions which contain lactose as the protector, IFN-β entrapped lyophilized liposome preparations with prescriptions shown in Table 8 were prepared to measure mean diameter and remaining ratio of DNA, as similar to Test Example 3. Results are shown in Tables 9 and 10. As seen therefrom, inhibition of liposome aggregation and DNA stabilizing effect can be recognized in all preparations with each of the prescriptions. The gene-entrapping lyophilized liposome preparations according to the invention do not show reduction in the amount of IFN-β expressed, even if the preparations were preserved for 12 months at 10 or −20° C., in any case of prescriptions 1–6 shown in Table 8. When the gene-entrapping liposomes were preserved in a state of solution at 10° C. as a control, the amount of IFN-β expressed reduced with preserved time. The lyophilized liposome samples show good restoration, when those are suspended into the aqueous solution of lactose. Added amounts of lactose correspond to 2667 g (Prescription 1), 3000 g (Prescription 2), 1200 g (Prescription 3), 900 g (Prescription 4), 600 g (Prescription 5) and 3333 g (Prescription 6), based on 1 g of the gene entrapped in the liposomes.

TABLE 8

| Prescription | Concentration of lactose (W/V %) | DNA concentration in liposomes μg/ml (lipid concentration: μmol/ml) |
|---|---|---|
| 1 | 8 | 30 (1.1) |
| 2 | 9 | 30 (1.1) |
| 3 | 9 | 75 (2.9) |
| 4 | 9 | 100 (3.8) |
| 5 | 9 | 150 (5.7) |
| 6 | 10 | 30 (1.1) |

TABLE 9

| Preservation temperature (° C.) | Prescription No. | Mean diameter (μm) | | | | | | |
|---|---|---|---|---|---|---|---|---|
| | | Before liophilization | Just after liophilization | After 4 months | After 6 months | After 8 months | After 10 months | After 12 months |
| 10 | 1 | 1.6 | 1.5 | 1.7 | 1.6 | 1.5 | 1.4 | 1.9 |
| | 2 | 1.9 | 1.7 | 1.2 | 1.4 | 1.3 | 1.4 | 0.9 |
| | 3 | 1.1 | 1.6 | 1.6 | 1.1 | 1.2 | 1.4 | 1.3 |
| | 4 | 1.1 | 1.9 | 1.7 | 1.3 | 1.6 | 1.5 | 1.7 |
| | 5 | 1.0 | 2.2 | 1.8 | 1.6 | 1.9 | 1.8 | 1.3 |
| | 6 | 1.4 | 2.3 | 1.4 | 1.9 | 1.5 | 2.1 | 1.5 |
| −20 | 1 | 1.6 | 1.5 | 1.8 | 1.8 | 1.5 | 1.8 | 1.4 |
| | 2 | 1.9 | 1.7 | 1.4 | 1.6 | 1.2 | 1.0 | 1.7 |
| | 3 | 1.1 | 1.6 | 1.1 | 1.2 | 1.0 | 1.4 | 1.1 |
| | 4 | 1.1 | 1.9 | 1.3 | 1.2 | 1.9 | 1.4 | 1.4 |
| | 5 | 1.0 | 2.2 | 1.4 | 1.8 | 2.0 | 1.4 | 1.7 |
| | 6 | 1.4 | 2.3 | 1.7 | 2.1 | 1.8 | 1.9 | 1.5 |

TABLE 10

| Preservation temperature (° C.) | Prescription No. | Ratio of DNA remained (%) | | | | | |
|---|---|---|---|---|---|---|---|
| | | Before liophilization | After 4 months | After 6 months | After 8 months | After 10 months | After 12 months |
| 10 | 1 | 100 | 100.5 | 98.2 | 99.5 | 97.7 | 96.9 |
| | 2 | 100 | 105.8 | 99.5 | 100.1 | 98.2 | 105.8 |
| | 3 | 100 | 96.3 | 99.7 | 100.1 | 99.2 | 98.5 |
| | 4 | 100 | 100.4 | 102.0 | 101.2 | 101.5 | 102.3 |
| | 5 | 100 | 99.0 | 97.9 | 99.8 | 98.1 | 96.3 |
| | 6 | 100 | 100.0 | 96.9 | 98.5 | 96.7 | 96.5 |
| −20 | 1 | 100 | 101.1 | 99.8 | 101.7 | 98.7 | 100.5 |
| | 2 | 100 | 102.1 | 100.2 | 101.6 | 105.8 | 105.8 |
| | 3 | 100 | 99.2 | 103.8 | 100.2 | 98.0 | 100.0 |
| | 4 | 100 | 101.8 | 100.0 | 101.5 | 94.9 | 100.6 |
| | 5 | 100 | 97.6 | 101.5 | 101.4 | 101.0 | 99.6 |
| | 6 | 100 | 101.2 | 99.5 | 99.5 | 97.4 | 99.4 |
| 10 (in solution) | — | 100 | 62.1 | 49.3 | 41.5 | 34.8 | 24.1 |

It has been apparent from results of the Test Examples that the gene-entrapping frozen liposome preparations according to the invention are stable over about 6 months in the minium wn der preservation temperature condition of −20° C., lyophilized liposome preparations are stable over 1 year in the minimum under preservation temperature condition in a range of −20~+10° C., and the liposomes show excellent restoration ability, when the liposomes are suspended in aqueous solution of disaccharide before preparing an actual preparation to be dosed.

What is claimed is:

1. A gene-entrapping liposome preparation, which comprises:
   liposomes wherein plasmid DNA is entrapped in said liposomes, and
   a disaccharide as a protector of said liposome and said plasmid DNA entrapped therein, which disaccharide is present at a concentration ranging from 300 to 3333 g per 1 g of said plasmid DNA entrapped in said liposomes,
   wherein the preparation is a frozen product obtained by freezing of the gene-entrapping liposome preparation during which cleavage of the plasmid DNA is prevented by the presence of said disaccharide added;
   said liposomes are of a diameter ranging from 0.6 to 6 μm; and
   constitutive lipids of said liposomes are N-(α-trimethylammonioacetyl)-didodecyl-D-glutamate chloride (TMAG), dilauroyl phosphatidylcholine (DLPC) and dioleoyl phosphatidylethanolamine (DOPE),
   whereby the plasmid DNA in the gene-entrapping liposome preparation remains uncleaved.

2. A gene-entrapping liposome preparation, which comprises:
   liposomes wherein plasmid DNA is entrapped in said liposomes, and
   a disaccharide as a protector of said liposome and said plasmid DNA entrapped therein, which disaccharide is present at a concentration ranging from 300 to 3333 g per 1 g of said plasmid DNA entrapped in said liposomes,
   wherein the preparation is a lyophilized product obtained by lyophilization of the gene-entrapping liposome preparation during which cleavage of the plasmid DNA is prevented by the presence of said disaccharide;
   said liposomes are of a diameter ranging from 0.6 to 6 μm; and
   constitutive lipids of said liposomes are N-(α-trimethylammonioacetyl)-didodecyl-D-glutamate chloride (TMAG), dilauroyl phosphatidylcholine (DLPC) and dioleoyl phosphatidylethanolamine (DOPE), whereby the plasmid DNA in the gene-entrapping liposome preparation remains uncleaved.

3. The gene-entrapping liposome preparation as claimed in claim 1 or 2, wherein said disaccharide is at least one of sucrose and lactose.

4. A process for preparing gene-entrapping liposome preparations, which comprises:

adding an aqueous solution of a disaccharide into gene-entrapping liposomes at a concentration ranging from 300 to 3333 g per 1 g of said gene entrapped in said liposomes to form said gene entrapping liposome preparation; and freezing or lyophilizing the gene-entrapping liposome preparation, wherein said liposomes are of a diameter ranging from 0.6 to 6 μm, and wherein cleavage of said gene-entrapped in said liposomes is prevented during the freezing or lyophilizing step by the presence of said disaccharide.

5. The process as claimed in claim 4, wherein constitutive lipids of said liposomes are N-(α-trimethylammonioacetyl)-didodecyl-D-glutamate chloride (TMAG), dilauroyl phosphatidylcholine (DLPC) and dioleoyl phosphatidylethanolamine (DOPE).

* * * * *